United States Patent [19]

Kober et al.

[11] Patent Number: 5,081,317
[45] Date of Patent: Jan. 14, 1992

[54] 1-BROMO-3-CHLORO-1,2-DIARYL-2-PROPANOLS, THE STEREO-SELECTIVE PREPARATION OF ERYTHRO-1-BROMO-3-CHLORO-1,2-DIARYL-2-PROPANOLS AND THE CONVERSION THEREOF INTO AZOLYLMETHYLOXIRANES

[75] Inventors: Reiner Kober, Fussgoenheim; Heinz Isak, Mutterstadt; Rainer Seele, Fussgoenheim, all of Fed. Rep. of Germany

[73] Assignee: BASF Aktiengesellschaft, Ludwigshafen, Fed. Rep. of Germany

[21] Appl. No.: 623,578

[22] Filed: Dec. 7, 1990

[30] Foreign Application Priority Data

Dec. 7, 1989 [DE] Fed. Rep. of Germany ....... 3940492

[51] Int. Cl.[5] ................. C07C 43/225; C07C 43/23; C07C 33/24
[52] U.S. Cl. ................. 568/645; 568/715; 568/807; 568/812
[58] Field of Search ............... 568/715, 812, 807, 645

[56] References Cited

U.S. PATENT DOCUMENTS 2,315,557  4/1940  Soday .................. 568/812
3,821,319  6/1974  Turner et al. .......... 568/807

Primary Examiner—Nicky Chan
Assistant Examiner—Margaret Argo
Attorney, Agent, or Firm—Oblon, Spivak, McClelland, Maier & Neustadt

[57] ABSTRACT

1-Bromo-3-chloro-1,2-diaryl-2-propanols of the general formula I

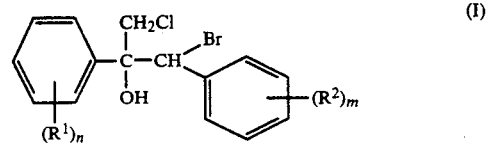

where n and m are each 1, 2 or 3, and $R^1$ and $R^2$ are each hydrogen, haloalkyl, alkoxy, haloalkoxy, t-butyl or an aromatic radical which may be substituted, are prepared and converted into azolylmethyloxiranes.

3 Claims, No Drawings

1-BROMO-3-CHLORO-1,2-DIARYL-2-PROPANOLS, THE STEREO-SELECTIVE PREPARATION OF ERYTHRO-1-BROMO-3-CHLORO-1,2-DIARYL-2-PROPANOLS AND THE CONVERSION THEREOF INTO AZOLYLMETHYLOXIRANES

The present invention relates to 1-bromo -3-chloro-1,2-diaryl-2-propanols of the general formula I

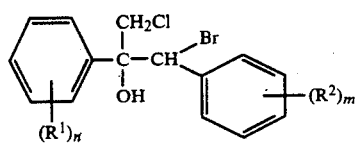

where n and m are each 1, 2 or 3, and $R^1$ and $R^2$ are each, independently of one another, hydrogen, halogen, $C_1$–$C_6$-haloalkyl, $C_1$–$C_5$-alkoxy, $C_1$–$C_5$-haloalkoxy, t-butyl or an aromatic radical which is unsubstituted or substituted once to three times by halogen, $C_1$–$C_5$-alkoxy $C_1$–$C_5$-haloalkoxy or t-butyl.

The present invention also relates to the preparation of the compounds I, in particular the stereoselective preparation of the compounds I with the erythro configuration, and the conversion thereof into azolylmethyloxiranes of the formula III

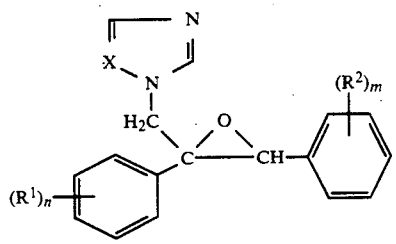

where the radicals have the abovementioned meanings, and X is CH or N.

It is disclosed in DE-A 32 18 129 and 33 18 130 that the azolylmethyloxiranes III have good antimycotic and fungicidal activity, and, in particular, the Z- or cis-oxiranes disclosed in EP-A 196 038 have pronounced fungicidal activity.

It is therefore an object of the present invention to prepare in the minimum number of steps and in high yield the azolylmethyloxiranes having the structure III in the cis configuration, with the intention of avoiding the conventional use of peroxides for the epoxidation.

We have now found that the 1-bromo-3-chloro-1,2-diaryl-2-propanols I defined in the first paragraph provide advantageous access to the azolylmethyloxiranes III.

Particularly suitable for the regioselective preparation of the azolylmethyloxiranes with the cis configuration are the propanols I with the erythro configuration, and the optical antipodes thereof, which are represented by Fischer projections Ia and Ib where Ar is aryl:

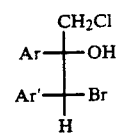

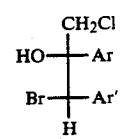

The 1-bromo-3-chloro-1,2-diaryl-2-propanols I are prepared according to the invention by radical bromination of chlorohydrins of the general formula II

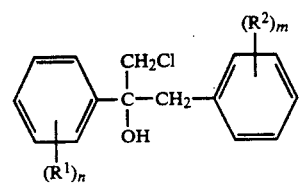

where $(R^1)_n$ and $(R^2)_m$ have the meanings specified for compound I, in an inert aprotic solvent.

We have found, surprisingly in view of the prior art, eg. Earl S. Huyser in Free-Radical Chain Reactions, Wiley-Interscience, 1970, pages 90 to 103, that the radical bromination stereoselectively forms the desired propanol I with the erythro configuration, the proportions of erythro and threo (see formulae Ia and Ib) found being from 3:1 to 7:1.

Surprisingly, a rearrangement of the intermediate β-phenylalkyl radical with migration of the $(R^1)_n$-substituted aryl, or an aryl shift in a possible tert-alkoxy radical (see loc. cit., page 253), is not found in practice. Likewise, virtually no elimination of water to give the diaryldihalopropenes disclosed in DE-A 32 10 570 is found.

It is possible to use for the radical bromination the conventional brominating reagents such as N-bromo derivatives of amides or imides. Examples are N-bromosuccinimide, 1,3-dibromo-5,5-dimethylhydantoin and N-bromophthalimide. It is also possible to use elemental bromine, bromotrichloromethane, bromopentachloroethane or tert-butyl hypobromite. It may be advantageous in some cases to add catalytic amounts of activators, such as iodobenzene, cobalt or copper(II) salts such as $CoBr_3$, $CuBr_2$, $PCl_3$, $PBr_3$ or quaternary ammonium bromides such as N-tetrabutylammonium bromide, to increase the reaction rate.

The amount of the brominating reagents is generally from 1 to 5, in particular 1 to 2, mole equivalents based on the chlorohydrin II.

The bromination can be carried out at from 0° to 100° C., preferably 10° to 80° C.

At low temperatures, eg. below 50° C., the radical chain reaction is carried out in the conventional manner for bromination reactions, by irradiating the reaction mixture with light. It may be advantageous in this case to add catalytic amounts of conventional radical initiators which, in addition to the photochemical cleavage, start up the radical chain process. Examples of suitable light sources are described in Houben-Weyl, Methoden der org. Chemie, volume 4/5a, pages 143 et seq.

In some cases the reaction can be initiated at above about 50° C. only with radical initiators, without additional irradiation.

Radical initiators which can be used are the conventional compounds of the azo or peroxide types such as tert-butyl peroxyneodecanoate, diacetyl peroxide, bis(2,4-dichlorobenzoyl) peroxide, diisopropyl peroxydicarbonate, dicyclohexyl peroxydicarbonate, acetylcyclohexanesulfonyl peroxide, dibenzoyl peroxide, dipropionyl peroxide, di-sec-butyl peroxydicarbonate, di-tert-butyl peroxydicarbonate, di(4-tert-butylcyclohexyl) peroxydicarbonate and azo-bis-isobutyronitrile.

The amount of the radical initiator is generally from 0.5 to 15 mol % based on chlorohydrin II. Larger amounts are possible but not usually necessary.

Typical temperatures for the bromination are those at which the radical initiator has a half-life of one hour, which is generally from about 30° to 80° C.

The aprotic solvents which can be used for the radical bromination are the conventional solvents mentioned, for example, in Houben-Weyl, Methoden der organischen Chemie, volume 4/5a, pages 143 et seq.. Examples of such solvents are halogenated aliphatic or aromatic hydrocarbons such as methylene chloride, tetrachloromethane, chlorobenzene, 1,2-dichloroethane, trichloroethylene, hexafluoroethane, and chlorofluorohydrocarbons such as 1,1-difluoro-1,2,2,2-tetrachloroethane, 1,1,1-trifluoro-2,2,2-trichloroethane or fluorinated hydrocarbons such as fluorobenzene or trifluoromethylbenzene.

Besides these preferred solvents, it is also possible to use hydrocarbons such as cyclohexane, n-pentane, n-hexane and benzene; nitrobenzene or nitriles such as propionitrile and acetonitrile, and carbon disulfide.

The amount of the solvent is not particularly critical. As a rule, the chlorohydrins of the formula II are diluted to 2 to 20% by weight solutions.

The chlorohydrins of the general formula II are known compounds which can be prepared by a benzyl Grignard reaction on ω-chloroacetophenones, eg. as described in DE-A 29 20 374, EP-B 15 756, DE-A 28 51 086 or EP-A 47 594.

The 1-bromo-3-chloro-1,2-diaryl-2-propanols I can be isolated from the crude reaction mixture in a conventional manner, e.g. by evaporating off the solvent and any excess bromine or by washing the organic phase with dilute alkali and evaporating the organic phase.

The proportions of erythro and threo isomers of the 1-bromo-3-chloro-1,2-diaryl-2-propanols I can be determined by, for example, HPLC (high-pressure liquid chromatography) or $^1$H-NMR methods, if necessary using the pure isomers for comparison. In the $^1$H-NMR spectrum the —CHBr—group gives a characteristic signal (singlet) which normally occurs at somewhat lower field in the case of the erythro configuration. The configuration can also be assigned by X-ray structural analysis, for example.

With regard to the biological activity of the final products III, the substituents $R^1$ and $R^2$ in the intermediate I according to the invention preferably have the following meanings: hydrogen; halogen such as fluorine, chlorine, bromine and iodine, preferably chlorine and fluorine; $C_1$-$C_6$-haloalkyl such as difluoromethyl, trifluoromethyl, trichloromethyl, pentafluoroethyl, preferably trifluoromethyl; $C_1$-$C_5$-alkoxy such as methoxy, ethoxy, propoxy, 1-methylethoxy, n-butoxy, tert-butoxy, 1-methylpropoxy, 2-methylpropoxy, preferably methoxy, ethoxy and propoxy; $C_1$-$C_5$-haloalkoxy such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, preferably trifluoromethoxy; tert-butyl; an aromatic radical, eg. phenyl which is unsubstituted or substituted by one to three radicals from the group comprising halogen $C_1$-$C_5$-alkoxy or $C_1$-$C_5$-haloalkoxy. it being possible for these radicals to have the meanings specified above for $R^1$ and $R^2$.

The indices n and m are preferably each 1 or 2, especially 1.

Examples of the substitution pattern in the 1-bromo-3-chloro-1,2-diaryl-2-propanols of the general formula I are listed in Table 1 which follows:

TABLE I

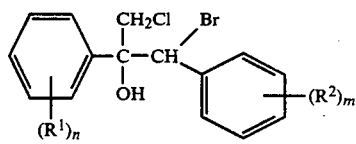

| Compound no. | $(R^1)_n$ | $(R^2)_m$ |
|---|---|---|
| 1 | 3-Cl | 3-Cl |
| 2 | 4-Cl | 2,4-diCl |
| 3 | 4-F | H |
| 4 | 4-F | 2-CF$_3$ |
| 5 | 4-F | 2-Cl |
| 6 | 4-H$_3$CO | 2-Cl |
| 7 | 4-Br | 2,4-diCl |
| 8 | 4-Cl | 2-CF$_3$—O |
| 9 | 4-C$_6$H$_5$ | 2-Cl |
| 10 | 4-Cl—C$_6$H$_4$ | H |
| 11 | 4-F | 3-C$_6$H$_5$ |
| 12 | 4-CF$_3$—O— | 2-Cl |
| 13 | H | H |
| 14 | H | 2-CF$_3$— |
| 15 | H | 2-CF$_3$—O |

The azolylmethyloxiranes III with fungicidal activity can be prepared advantageously starting from the 1-bromo-3-chloro-1,2-diaryl-2-propanols I according to the invention, employing the isomers of the formula Ia and Ib with the erythro configuration for the preparation of the preferred cis-azolylmethyloxiranes in which the aryl groups are located transoid with respect to one another.

Accordingly, the present invention provides a process for the preparation of azolylmethyloxiranes of the formula III

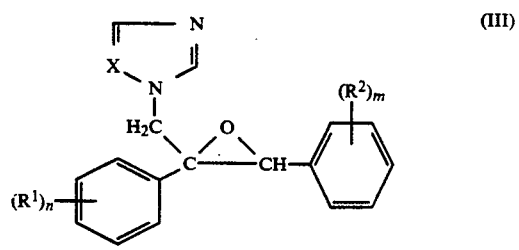

where $(R^1)_n$ and $(R^2)_m$ have the meanings specified in claim 1, and X is CH or N, which comprises reacting 1-bromo-3-chloro-1,2-diaryl-2-propanols of the formula I with 1,2,4-triazole or imidazole in the presence of a base or directly with the 1,2,4-triazolide or the imidazolide in an inert solvent.

The reaction of the 1-bromo-3-chloro-1,2-diaryl-2-propanols I with 1,2,4-triazole or imidazole in the presence of a base surprisingly takes place regioselectively to give the azolylmethyloxiranes of the formula III, there being virtually exclusive substitution on the chloromethyl group in the compound I, and formation of the oxirane ring in situ by inverse intramolecular substitution of the hydroxyl. The oxirane formation generally takes place somewhat more rapidly than the substitution by the triazolide or imidazolide so that, depending on how the reaction is carried out, the chloromethyloxirane IV

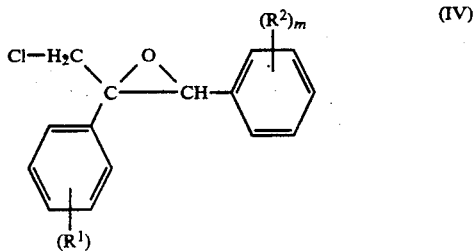

which occurs as an intermediate at least in some cases, can be isolated and subsequently converted by reacting with the 1,2,4-triazolide or imidazolide into the final product III. However, the reaction is advantageously carried out to give the azolylmethyloxirane III directly, without isolation of IV.

The substitution reaction can be represented by the following equations, in which Me is a metal atom:

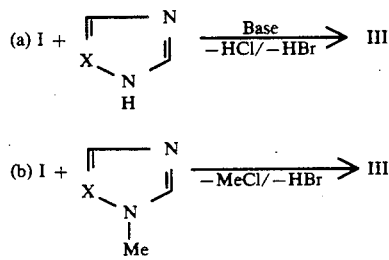

Reaction a) is carried out in the presence or absence of a solvent or diluent, with the addition of 2 to 3 mole equivalents of an inorganic or organic base and with or without the addition of a reaction accelerator.

The preferred solvents or diluents include ketones such as acetone, methyl ethyl ketone or cyclohexanone, nitriles such as acetonitrile, esters such as ethyl acetate, ethers such as diethyl ether, tetrahydrofuran or dioxane, sulfoxides such as dimethyl sulfoxide, amides such as dimethylformamide, dimethylacetamide or N-methylpyrrolidone, and sulfolane or mixtures thereof.

Examples of suitable bases, which can also be used as acid acceptors in the reaction, are alkali metal hydroxides such as lithium, sodium or potassium hydroxide, alkali metal carbonates such as sodium or potassium carbonate or sodium or potassium bicarbonate, or excess 1,2,4-triazole. However, it is also possible to use other conventional bases such as alkali metal hydrides or amides and, in particular, alcoholates eg. sodium methylate or sodium or potassium tert-butylate.

Suitable and preferred reaction accelerators are metal halides such as sodium iodide or potassium iodide, quaternary ammonium salts such as tetrabutylammonium chloride, bromide or iodide, benzyltriethylammonium chloride or bromide or crown ethers such as 12-crown-4, 15-crown-5, 18-crown-6, dibenzo-18-crown-6 or dicyclo-hexano-18-crown-6.

The reaction is generally carried out at from 20° to 110° C., under atmospheric or superatmospheric pressure, continuously or batchwise.

Where Me is a metal atom, the reaction is carried out in the presence or absence of a solvent or diluent and with or without the addition of a strong inorganic or organic base. Examples of metals are sodium and potassium.

Examples of suitable bases, which can also be used as acid acceptors in the reaction, are alkali metal hydrides such as lithium, sodium and potassium hydride, alkali metal amides such as those of sodium and potassium, and triphenylmethyllithium, -sodium or -potassium and naphthyllithium, -sodium or -potassium and, in particular, alcoholates such as sodium or potassium tertbutylate or sodium methylate.

Suitable diluents for reaction b) are polar organic solvents such as nitriles, e.g. acetonitrile, sulfoxides, e.g. dimethyl sulfoxide, formamides, e.g. dimethylformamide, ketones, e.g. acetone, ethers, e.g. diethyl ether and tetrahydrofuran and, in particular, chlorohydrocarbons, e.g. methylene chloride and chloroform.

The reaction is generally carried out at from 0° to 100° C., preferably at from 50° to 80° C. The triazole is generally used in an amount of from 1 to 3, in particular 1 to 1.5, mole equivalents based on the chlorohydrin II. The amount of base is normally from 2 to 5, in particular 2 to 2.5, mole equivalents based on chlorohydrin II.

When triazolides, e.g. sodium triazolide, are used, acting both as base and as reactant, it is possible to employ, for example, 2 to 3 mole equivalents based on II.

In an advantageous embodiment of the process, the cis- or Z-azolylmethyloxiranes IIIa

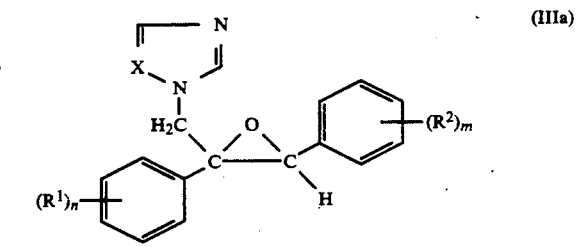

are prepared regio- and stereoselectively starting from the 1-bromo-3-chloro-1,2-diaryl-2-propanols Ia and Ib with the erythro configuration.

The trans- or E-azolylmethyloxiranes III are obtained correspondingly from the small proportions of 1-bromo-3-chloro-1,2-diaryl-2-propanols I with the threo configuration in the reaction mixture.

The individual steps in the synthesis are explained in the examples which follow.

EXAMPLE 1

Preparation of the Starting Materials II by Grignard Reactions

1-Chloro-3-(2-chlorophenyl)-2-(4-fluorophenyl)-2-propanol 30 g (1.25 mol) of magnesium turnings are introduced into 100 ml of diethyl ether at room temperature, and 17 g (0.1 mol) of 2-chlorobenzyl chloride are added dropwise within 4 to 5 minutes. After the Grignard reaction has started, a further 153 g (0.95 mol) of 2-chlorobenzyl chloride in 800 ml of diethyl ether are added dropwise at the reflux temperature within about one hour. After a further 30 minutes, the Grignard solution is cooled and added dropwise at 0° to 2° C. to 157 g (0.91 mol) of 4-fluoro-ω-chloroacetophenone in 250 ml of toluene, and the mixture is then stirred at 0° C. for 1 to 2 hours and worked up in a conventional manner.

EXAMPLE 2

Preparation of the 1-bromo-3-chloro-1,2-diaryl-2-propanols I by photobromination 1-Bromo-3-chloro-1-(2-chlorophenyl)-2-(4-fluorophenyl)-2-propanol (compound no. 5 from Table 1)

4.0 g (13.4 mmol) of 1-chloro-3-(2-chlorophenyl)-2-(4-fluorophenyl)-2-propanol are photobrominated with 2.3 g (8.0 mmol) of 1,3-dibromo-5,5-dimethylhydantoin in 80 ml of tetrachloromethane at 35° C. while stirring vigorously and irradiating with mixed light from an Osram HWL 235 V/500 W lamp. The hydantoin is filtered off with suction, the filtrate is extracted with dilute sodium carbonate solution and water, and conventional working up provides 5.1 g of crude product as an oil which is employed for the next stage. The erythro:threo isomer ratio found from the signals for the —CHBr— groups in the $^1$H-NMR spectrum, which appear at 6.4 ppm for the erythro compounds and at 6.2 ppm for the threo compound (each measured in CDCl$_3$), is 4:1. The erythro isomer is also characterized by a doublet of doublets at 4.1 ppm.

EXAMPLE 3

Conversion of 1-bromo-3-chloro-1,2-diaryl-2-propanols I into azolylmethyloxiranes III cis-2-(1,2,4-triazol-1-ylmethyl)-3-(2-chlorophenyl)-2-(4-fluorophenyl)oxirane 3.9 g (10.4 mmol) of the crude 1-bromo-3-chloro-1-(2-chlorophenyl)-2-(4-fluorophenyl)-2-propanol prepared above are stirred in 15 ml of dimethylformamide with 2.4 g (26.4 mmol) of sodium 1,2,4-triazolide at 75° C. for 4 hours. The reaction mixture is then neutralized with glacial acetic acid and diluted with about 15 to 20 ml of water, stirring vigorously, when cis-2-(1,2,4-triazol-1-ylmethyl)-3-(2-chlorophenyl)-2-(4-fluorophenyl)oxirane separates out as crude crystals. Filtration with suction, washing with DMF/water (1:1) and boiling the residue with a little n-pentane and cyclohexane provide, after drying, 1.85 g of the desired product as colorless crystals (about 58% yield).

EXAMPLE 4

Preparation of 1-bromo-3-chloro-1,2-diaryl-2-propanols I by bromination in the presence of a radical initiator 1-Bromo-3-chloro-1-(2-chlorophenyl)-2-(4-fluorophenyl)-2-propanol 2.29 g (8.0 mmol) of 1,3-dibromo-5,5-dimethylhydantoin and 0.2 g of azo-bis-isobutyronitrile (Phorophor N) are added to 4.0 g (13.4 mmol) of 1-chloro-3-(2-chlorophenyl)-2-(4-fluorophenyl)-2-propanol in 40 ml of dichloroethane under dry nitrogen or carbon dioxide, and the mixture is stirred at 72° to 74° C. for 10 hours, adding a further 0.2 g of Phorophor N after 5 hours. The working up is carried out as indicated for the photobromination in Example 2. The yield of crude product, which still contains a small amount of solvent, is 6.2 g, and the erythro:threo isomer ratio is about 3:1.

We claim:

1. A 1-bromo-3-chloro-1,2-diaryl-2-propanol of the formula I

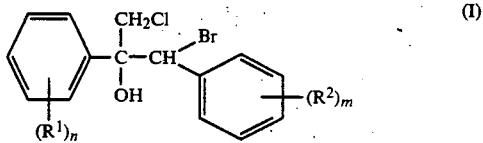

where n and m are each 1, 2 or 3, and $R^1$ and $R^2$ are each, independently of one another, hydrogen, halogen, $C_1$–$C_6$-haloalkyl, $C_1$–$C_5$-alkoxy, $C_1$–$C_5$-haloalkoxy, t-butyl or phenyl which is unsubstituted or substituted once to three times by halogen, $C_1$–$C_5$-alkoxy, $C_1$–$C_5$-haloalkoxy or t-butyl.

2. An erythro-1-bromo-3-chloro-1,2-diaryl-2-propanol of the formula I as claimed in claim 1, where $(R^1)_n$ is hydrogen or 4-halo and $(R^2)_m$ is 2-trifluoromethyl or 2-halo.

3. An erythro-1-bromo-3-chloro-1,2-diaryl-2-propanol of the formula I as claimed in either of claims 1 and 2, where $R^1$ is 4-fluoro and $R^2$ is 2-trifluoromethyl, 2-chloro or 2-bromo.

* * * * *